United States Patent
Haering et al.

(10) Patent No.: US 8,278,077 B2
(45) Date of Patent: Oct. 2, 2012

(54) ENZYMATIC PRODUCTION OF (METH)ACRYLIC ACID ESTERS

(75) Inventors: Dietmar Haering, Neu-Edingen (DE);
Uwe Meisenburg, Mannheim (DE);
Bernhard Hauer, Fussgoenheim (DE);
Frank Dietsche, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 687 days.

(21) Appl. No.: 11/995,628

(22) PCT Filed: Jul. 31, 2006

(86) PCT No.: PCT/EP2006/064848
§ 371 (c)(1),
(2), (4) Date: Jan. 14, 2008

(87) PCT Pub. No.: WO2007/014935
PCT Pub. Date: Feb. 8, 2007

(65) Prior Publication Data
US 2008/0200631 A1    Aug. 21, 2008

(30) Foreign Application Priority Data
Aug. 4, 2005   (DE) .................. 10 2005 037 430

(51) Int. Cl.
*C12P 7/62* (2006.01)
*C07C 67/03* (2006.01)
*C07C 69/52* (2006.01)
(52) U.S. Cl. .................. 435/135; 560/217; 560/225
(58) Field of Classification Search .................. None
See application file for complete search history.

(56) References Cited

U.S. PATENT DOCUMENTS

| | | | |
|---|---|---|---|
| 3,254,115 A * | 5/1966 | Cohen et al. .................. 560/225 |
| 5,214,077 A | 5/1993 | Herzig et al. | |
| 5,240,835 A | 8/1993 | Pettrone et al. | |
| 102,671 A1 | 8/2002 | Janda et al. | |

FOREIGN PATENT DOCUMENTS

| | | |
|---|---|---|
| EP | 457 332 | 11/1991 |
| EP | 0 508 491 | 10/1992 |
| EP | 566 095 | 10/1993 |
| EP | 0 999 299 A1 | 5/2000 |
| GB | 465789 | 5/1937 |
| GR | SU 276046 | 12/1970 |
| WO | WO 03/042227 A2 | 5/2003 |
| WO | WO 2005/059151 | 6/2005 |

OTHER PUBLICATIONS

Ness et al, Journal of the American Chemical Society, The Enol Content of some beta-Keto Esters, 1938, 60 (9), pp. 2213-2215.*
Gilazhov, E.G., "Synthesis of unsaturated esters of cyclic and heterocyclic acetylenic alcohols and their linear polymers", Abstract XP 002401968, 1986.
Burgess et al., "Biocatalytic Resolutions of α-Methyleneβ-Hydroxy Esters and Ketones", Journal of Org. Chem., vol. 55, No. 4, 1990, pp. 1138-1139, XP 002401966.
Waldinger et al., "Aryl Propargylic Alcohols of High Enantiomeric Purity via Lipase Catalyzed Resolutions", Tetrahedron: Asymmetry, vol. 7, No. 5, pp. 1485-1488, XP 004047709, 1996.
Lie Ken Jie et al., "Lipase Specificity Toward Some Acetylenic and Olefinic Alcohols in the Esterification of Pentanoic and Stearic Acids, Lipids", vol. 33, No. 9, pp. 861-867, XP 008069811, 1998.
Warwel et al., "An Efficient Method for Lipase-Catalysed Preparation of Acrylic and Methacrylic Acid Esters", Biotechnology Techniques, vol. 10, No. 4, pp. 283-286, XP 008069801, Apr. 1996.
U.S. Appl. No. 12/743,819, filed May 20, 2010, Haering et al.
Vilas Athawale, et al., "Mild Chemo-Enzymatic Synthesis of Polymer-Supported Cinchona Alkaloids and Their Application in Asymmetric Michael Addition", Tetrahedron Letters 42 (2001), pp. 4541-4543.
A. Ghogare, et al., "Oxime Esters As Novel Irreversible ACYL Transfer Agents for Lipase Catalysis in Organic Media" J. Chem. Soc., Chem. Communication, 1989, pp. 1533-1535.
V.D. Athawale, et al., "Chemoenzymatic Syntheses of Optically Active Polyacrylates", Macromolecules 1999, 32, pp. 6065-6068.
Daniel F. Harvey, et al., Cyclization Reactions of Molybdenum and Chromium Carbene Complexes With 1, 6- and 1,7-Enynes: Effect of Tether Length and Composition., J.Am. Chem. Soc. 1992, 114, pp. 8424-8434.
Rajesh Kumar, et al., Biocatalytic Route to Well-Defined Macromers Built Around a Sugar Core, vol. 124, No. 9, 2002, J.AM. Chem. Soc. pp. 1850-1851.
A.T.J.W. De Goede, et al., "Selective Lipase-Catalyzed Esterification of Alkyle Glycosides", Biocatalysis, 1994, vol. 9, pp. 145-155.
Houben-Weyl, Methoden Der Organischen Chemie, vol. V/2a, Thieme Verlag 1977, pp. 282-335 ff.

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

The present invention relates to a process for preparing (meth)acrylic esters of alcohols having C—C triple bonds, to processes for their preparation, and to their use.

9 Claims, No Drawings

ENZYMATIC PRODUCTION OF (METH)ACRYLIC ACID ESTERS

CROSS-REFERENCE TO RELATED APPLICATIONS

The present application is a 35 U.S.C. §371 National Stage patent application of International patent application PCT/EP06/064848, filed on Jul. 31, 2006, which claims priority to German patent application DE 102005037430.1, filed on Aug. 4, 2005.

The present invention relates to a process for preparing (meth)acrylic esters of alcohols having C—C triple bonds, to processes for their preparation, and to their use.

(Meth)acrylic esters are generally prepared by acid- or base-catalyzed esterification of (meth)acrylic acid or transesterification of other (meth)acrylic esters with alcohols, or by reaction of alcohols with (meth)acryloyl chloride in the presence of bases.

(Meth)acrylic esters of alcohols having C—C triple bonds are known in principle. In the conventional esterification of such alcohols with acids, for example, acid-induced side reactions, especially isomerizations of the triple bond, lead nevertheless to product mixtures which are usually inhomogeneous, or at least are strongly colored.

Similarly to what is the case with the migration of C—C double bonds as a result of allyl rearrangement, the C—C triple bond in alkynes is able to migrate (alkyne-allene rearrangement). Isomerizations of this kind are often equilibrium reactions. Rearrangement takes place, for example, by migration of an anion or cation, and is catalyzed by acids or bases (Houben-Weyl, Methoden der organischen Chemie vol. V/2a, Thieme Verlag 1977, page 282 ff). As a result of this instability on the part of the triple bond, alkynes tend under acidic or basic conditions to form by-products (e.g., allenes and their derivatives), which have to be removed from the reaction mixture, by distillation or extraction, which is costly and inconvenient.

In EP 508491 (Wacker Chemie, 1992) 2-propynoxyethanol was azeotropically esterified with acrylic acid in toluene as azeotrope former, with catalysis by sulfuric acid. After 4 h at 120° C. the excess acrylic acid was neutralized with NaHCO$_3$ and washed out with water. Toluene was then distilled off and 2-propargyloxyethyl acrylate was purified by distillation. This gave a pale yellowish product, with an 85% yield.

In the case of base-catalyzed transesterification or other syntheses, as with metal complexes, for example, for the same reason, the products are mixtures which are likewise complex and colored. In order to remove coloration and unconverted reactants it is necessary to work up the product mixtures, by means of costly and inconvenient alkaline washes.

The preparation of acryloyl chloride in the presence of bases is likewise known:

U.S. Pat. No. 3,254,115 (Thiokol Chemical Corp., 1966) describes the preparation of propargyl acrylate from propargyl alcohol and acryloyl chloride. The catalyst is triethylamine, and the solvent used is benzene. The product was distilled under reduced pressure, with a 60% yield.

Harvey et al. (J. Am. Chem. Soc., 1992, 114, 8424-8434) prepare propargyl acrylate again from propargyl alcohol and acryloyl chloride. The catalyst is triethylamine and the solvent used is dichloromethane. The product is extracted a number of times in succession with HCl, NaHCO$_3$, and water with a 90% yield.

The preparation of (meth)acrylic esters by an enzymatic esterification or transesterification is known.

Kumar and Gross describe in J. Am. Chem. Soc. 2002, 124, 1850-1851 the lipase-catalyzed conversion of isopropylidene-protected sugars by reaction with vinyl methacrylate. Complete conversion is achieved by means of the specific reactant, vinyl methacrylate, since vinyl alcohol liberated is withdrawn from the reaction equilibrium as acetaldehyde. A disadvantage of this process is that vinyl methacrylate, as a specialty monomer, is expensive and is available commercially only in small quantities.

A. T. J. W. de Goede et al. describe in Biocatalysis, 1994, 9, 145-155 the transesterification of α-O-octylglucoside with ethylacrylate to form the 6-O-acrylic ester in the presence of lipases. Disadvantages of this process are that it is restricted to glucosides and glycosidic bonds and reacts sensitively to steric influences in the glucoside. Moreover, products with relatively high degrees of acrylation are obtained, owing to unselective side reactions.

EP-A1 999 229 describes the enzymatic esterification and transesterification of polyoxyalkylenes with (meth)acrylic acid and (meth)acrylic esters.

WO 03/042227 discloses the lipase-catalyzed transesterification of alkyl acrylates with sugars.

U.S. Pat. No. 5,240,835 describes the transesterification of alkyl acrylates with alcohols under catalysis by a biocatalyst from *Corynebacterium oxydans*. Exemplified therein is the reaction of a 96-fold molar excess of ethyl acrylate with 2,2-dimethyl-1,3-propanediol. The yield, after 3 days at 30° C., was only 21%.

Athawale and Manjrekar (Tetrahedron Lett. 2001, 42 4541-4543) describe the lipase-catalyzed acrylation of alkaloids using 2,3-butanedione monooxime acrylate. The monomer was polymerized and used for inducing enantioselective Michael addition.

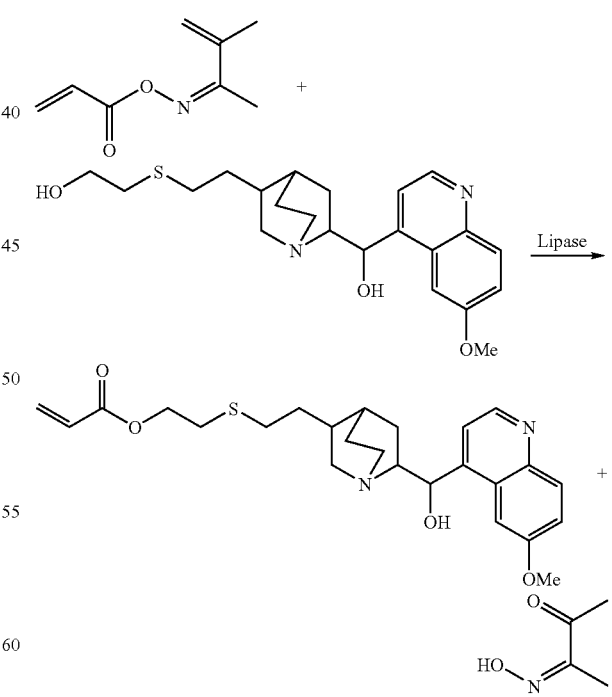

Athawale and Gaonkar (Macromolecules 1999, 32, 6065-6068) describe the lipase-catalyzed acrylation of 2-phenylethanols using 2,3-butanedione monooxime acrylate. The monomer was subsequently polymerized.

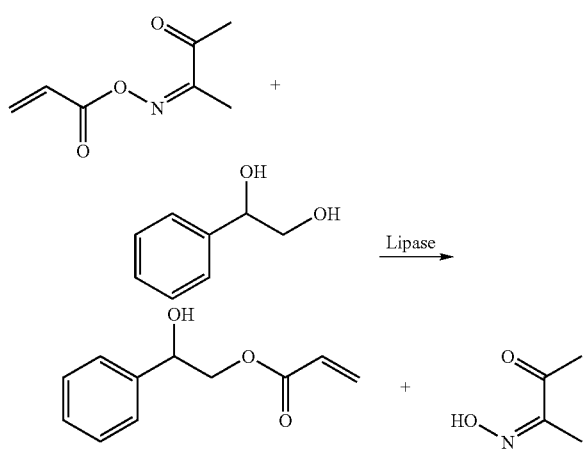

Ghogare and Kumar (J. Chem. Soc. 1989, 1533-1535) describe the lipase-catalyzed acrylation of various alcohols, including 2-ethylhexane-1,3-diol, with an activated 2,3-butanedione monooxime acrylate.

A frequent disadvantage of these reactions is the need to use activated acrylates, such as the oximes or vinyl esters, which are expensive and difficult to acquire industrially.

It was an object of the present invention to provide a process with which (meth)acrylic esters of alcohols having C—C triple bonds can be prepared in good yield and with low color numbers from simple reactants. The synthesis ought to proceed under mild conditions, giving products having a low color number and high purity. The use of acidic or basic catalysts ought specifically to be avoided, in order to prevent by-products arising. As a result of that it is possible to forego costly and inconvenient distillative or extractive product purification. Moreover, it should be unnecessary to use expensive, activated (meth)acrylic acid derivatives, such as monooximes or vinyl(meth)acrylate, for example.

This object has been achieved by a process for preparing (meth)acrylic esters (F) of alcohols having at least one C—C triple bond, by subjecting at least one alcohol having at least one C—C triple bond to esterification with (meth)acrylic acid or to transesterification with at least one (meth)acrylic ester (D) in the presence of at least one enzyme (E).

With the aid of the process of the invention it is possible to prepare such (meth)acrylic esters (F) in higher chemical and space-time yield under mild conditions with good color numbers, with no need for protective-group operations, and using simple starting materials.

(Meth)acrylic acid stands in this text for methacrylic acid and acrylic acid, preferably for acrylic acid.

Alcohols (C) suitable in accordance with the invention are alcohols comprising at least one C—C triple bond and at least one hydroxyl group.

Such alcohols may for example comprise 1 to 3, preferably 1 or 2, and more preferably exactly one C—C triple bond.

The alcohols (C) may comprise one to six, preferably one to four, more preferably one to three, very preferably one or two, and in particular precisely one hydroxyl group.

The alcohols (C) useful in accordance with the invention may further comprise other heteroatoms, examples being nitrogen and/or sulfur atoms, but are preferably constructed only of carbon, hydrogen and oxygen atoms.

The alcohols (C) useful in accordance with the invention may further comprise other functional groups, examples being C—C double bonds or amino, carboxyl, ether or carboxylic ester groups. Apart from the C—C triple bond and the hydroxyl group they preferably comprise no other functional groups.

The hydroxyl groups of the alcohols (C) useful in accordance with the invention may be primary, secondary or tertiary, preference being given to those having primary or secondary hydroxyl groups and particular preference to those having primary hydroxyl groups. In addition, different hydroxyl groups, primary and secondary for example, may be present simultaneously in the alcohol.

Primary hydroxyl groups are hydroxyl groups attached to precisely one carbon atom which is connected to precisely one other carbon atom. Similarly, for secondary hydroxyl groups, the carbon atom attached to them is joined, correspondingly, to two carbon atoms, and in the case of tertiary hydroxyl groups to three carbon atoms.

Preferred alcohols (C) are of the formula (1)

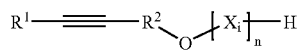

in which
$R^1$ is hydrogen, $C_1$-$C_{18}$ alkyl, $C_2$-$C_{18}$ alkyl uninterrupted or interrupted by one or more oxygen and/or sulfur atoms and/or by one or more substituted or unsubstituted imino groups, or is $C_6$-$C_{12}$ aryl, $C_5$-$C_{12}$ cycloalkyl or a five- to six-membered heterocycle containing oxygen, nitrogen and/or sulfur atoms, it being possible for each of the stated radicals to be substituted by aryl, alkyl, aryloxy, alkyloxy, heteroatoms and/or heterocycles, and
$R^2$ is a $C_1$-$C_{20}$ alkylene, $C_5$-$C_{12}$ cycloalkylene or $C_6$-$C_{12}$ arylene or $C_2$-$C_{20}$ alkylene interrupted by one or more oxygen and/or sulfur atoms and/or by one or more substituted or unsubstituted imino groups and/or by one or more cycloalkyl, —(CO)—, —O(CO)O—, —(NH)(CO)O—, —O(CO)(NH)—, —O(CO)— or —(CO)O groups, it being possible for each of the stated radicals to be substituted by aryl, alkyl, aryloxy, alkyloxy, heteroatoms and/or heterocycles,
n is an integer 0 to 3, preferably 0 to 2, and more preferably 1 to 2, and
$X_i$ for each i=0 to n can be selected, independently of one another, from the group —$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—O—, —$CH_2$—CHPh-O— and —CHPh-$CH_2$—O—, preferably from the group —$CH_2$—$CH_2$—O—, —$CH_2$—$CH(CH_3)$—O— and —$CH(CH_3)$—$CH_2$—O—, and more preferably —$CH_2$—$CH_2$—O—,
in which Ph is phenyl and Vin is vinyl.

Particularly preferred alcohols (C) are of the formula (2)

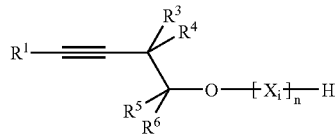

in which
n, $X_i$ and $R^1$ can be as defined above and
$R^3$ to $R^6$ independently of one another are hydrogen, $C_1$-$C_{18}$ alkyl, $C_2$-$C_{18}$ alkyl uninterrupted or interrupted by one or more oxygen and/or sulfur atoms and/or by one or more substituted or unsubstituted imino groups, or are $C_6$-$C_{12}$ aryl, $C_5$-$C_{12}$ cycloalkyl or a five- to six-membered heterocycle having oxygen, nitrogen and/or sulfur atoms, it being possible for each of the stated radicals to be substituted by aryl, alkyl, aryloxy, alkyloxy, heteroatoms and/or heterocycles.

Very particular preference is given to alcohols (C) of the formula (3)

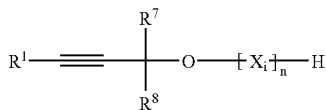

in which n, $X_i$ and $R^1$ can be as defined above and $R^7$ and $R^8$ independently of one another are hydrogen, $C_1$-$C_{18}$ alkyl, $C_2$-$C_{18}$ alkyl uninterrupted or interrupted by one or more oxygen and/or sulfur atoms and/or by one or more substituted or unsubstituted imino groups, or are $C_6$-$C_{12}$ aryl, $C_5$-$C_{12}$ cycloalkyl or a five- to six-membered heterocycle having oxygen, nitrogen and/or sulfur atoms, it being possible for each of the stated radicals to be substituted by aryl, alkyl, aryloxy, alkyloxy, heteroatoms and/or heterocycles, in which $R^7$ and $R^8$ may also together form a ring.

In the above definitions $C_1$-$C_{20}$ alkylene unsubstituted or substituted by aryl, alkyl, aryloxy, alkyloxy, heteroatoms and/or heterocycles is for example methylene, 1,1-ethylene, 1,2-ethylene, 1,1-propylene, 1,2-propylene, 1,3-propylene, 1,1-butylene, 1,2-butylene, 1,3-butylene, 1,4-butylene, 1,6-hexylene, 2-methyl-1,3-propylene, 2-ethyl-1,3-propylene, 2,2-dimethyl-1,3-propylene or 2,2-dimethyl-1,4-butylene, $C_5$-$C_{12}$ cycloalkylene unsubstituted or substituted by aryl, alkyl, aryloxy, alkyloxy, heteroatoms and/or heterocycles is for example cyclopropylene, cyclopentylene, cyclohexylene, cyclooctylene or cyclododecylene, $C_2$-$C_{20}$ alkylene unsubstituted or substituted by aryl, alkyl, aryloxy, alkyloxy, heteroatoms and/or heterocycles and uninterrupted or interrupted by one or more oxygen and/or sulfur atoms and/or by one or more substituted or unsubstituted imino groups and/or by one or more cycloalkyl, —(CO)—, —O(CO)O—, —(NH)(CO)O—, —O(CO)(NH)—, —O(CO)— or —(CO)O groups is for example 1-oxa-1,3-propylene, 1,4-dioxa-1,6-hexylene, 1,4,7-trioxa-1,9-nonylene, 1-oxa-1,4-butylene, 1,5-dioxa-1,8-octylene, 1-oxa-1,5-pentylene, 1-oxa-1,7-heptylene, 1,6-dioxa-1,10-decylene, 1-oxa-3-methyl-1,3-propylene, 1-oxa-3-methyl-1,4-butylene, 1-oxa-3,3-dimethyl-1,4-butylene, 1-oxa-3,3-dimethyl-1,5-pentylene, 1,4-dioxa-3,6-dimethyl-1,6-hexylene, 1-oxa-2-methyl-1,3-propylene, 1,4-dioxa-2,5-dimethyl-1,6-hexylene, 1-oxa-1,5-pent-3-enylene, 1-oxa-1,5-pent-3-ynylene, 1,1-, 1,2-, 1,3- or 1,4-cyclohexylene, 1,2- or 1,3-cyclopentylene, 1,2-, 1,3- or 1,4-phenylene, 4,4'-biphenylene, 1,4-diaza-1,4-butylene, 1-aza-1,3-propylene, 1,4,7-triaza-1,7-heptylene, 1,4-diaza-1,6-hexylene, 1,4-diaza-7-oxa-1,7-heptylene, 4,7-diaza-1-oxa-1,7-heptylene, 4-aza-1-oxa-1,6-hexylene, 1-aza-4-oxa-1,4-butylene, 1-aza-1,3-propylene, 4-aza-1-oxa-1,4-butylene, 4-aza-1,7-dioxa-1,7-heptylene, 4-aza-1-oxa-4-methyl-1,6-hexylene, 4-aza-1,7-dioxa-4-methyl-1,7-heptylene, 4-aza-1,7-dioxa-4-(2'-hydroxyethyl)-1,7-heptylene, 4-aza-1-oxa-(2'-hydroxyethyl)-1,6-hexylene or 1,4-piperazinylene, $C_6$-$C_{12}$ arylene unsubstituted or substituted by aryl, alkyl, aryloxy, alkyloxy, heteroatoms and/or heterocycles is for example 1,2-, 1,3- or 1,4-phenylene, 4,4'-biphenylene, tolylene or xylylene, $C_1$-$C_{18}$ alkyl, or $C_2$-$C_{18}$ alkyl uninterrupted or interrupted by one or more oxygen and/or sulfur atoms and/or by one or more substituted or unsubstituted imino groups, is for example methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hetadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, tri-chloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and preferably methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hetadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, 2-cyanoethyl, 2-cyanopropyl, chloromethyl, 2-chloroethyl, trichloromethyl, trifluoromethyl, 1,1-dimethyl-2-chloroethyl, and 2,2,2-trifluoroethyl, $C_6$-$C_{12}$ aryl uninterrupted or interrupted by one or more oxygen and/or sulfur atoms and/or by one or more substituted or unsubstituted imino groups is for example phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxy-methylphenyl, and preferably phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, chloronaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, $C_5$-$C_{12}$ cycloalkyl uninterrupted or interrupted by one or more oxygen and/or sulfur atoms and/or by one or more substituted or unsubstituted imino groups is for example cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl, and also a saturated or unsaturated bicyclic system such as norbornyl or norbornenyl, and preferably cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, chlorocyclohexyl, dichlorocyclohexyl, dichlorocyclopentyl, and also a saturated or unsaturated bicyclic system such as norbornyl or norbornenyl
and five- to six-membered heterocycle having oxygen, nitrogen and/or sulfur atoms and uninterrupted or interrupted by one or more oxygen and/or sulfur atoms and/or by one or more substituted or unsubstituted imino groups is for example furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl.

Examples of $R^2$ are methylene, 1,1-ethylene, 1,2-ethylene, 1,1-propylene, 2,2-propylene, 1,2-propylene, 1,3-propylene, 1,1-dimethyl-1,2-ethylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, 3-methyl-1,5-pentylene, 3,5-heptylene, 1,2-cyclopentylene, 1,3-cyclopentylene, 1,2-cyclohexylene, 1,3-cyclohexylene and orthophenylene, preferably methylene, 1,1-ethylene, 1,2-ethylene, 1,1-propylene and 2,2-propylene, more preferably methylene, 1,1-ethylene, 1,2-ethylene and 2,2-propylene, and very preferably methylene.

Preferred examples of $R^1$ and $R^3$ to $R^7$ are, independently of one another, hydrogen, $C_1$-$C_4$ alkyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, phenyl, naphthyl or benzyl. $R^1$ and $R^3$ to $R^7$ independently of one another are preferably hydrogen and methyl, more preferably hydrogen.

$C_1$-$C_4$ alkyl for the purposes of this text denotes methyl, ethyl, isopropyl, n-propyl, n-butyl, isobutyl, sec-butyl or tert-butyl, preferably methyl, ethyl, n-propyl, and n-butyl, more preferably methyl, ethyl, and n-butyl, very preferably methyl and ethyl, and especially methyl.

Preferred examples of alcohols (C) are 3-methyl-1-pentyn-3-ol, 2-propyn-1-ol (propargyl alcohol), 3-butyn-2-ol, 2-methyl-3-butyn-2-ol, 4-pentyn-1-ol, 1-ethynylcyclohexanol, 3-butyn-1-ol, 2-butyn-1-ol and 1-octyn-3-ol, and their mono- or di-ethoxylated products. Particular preference is given to 2-propyn-1-ol (propargyl alcohol), 2-butyn-1-ol, 3-butyn-2-ol, and 2-methyl-3-butyn-2-ol, and their mono- or di-ethoxylated products, very particular preference to 2-propyn-1-ol (propargyl alcohol) and its mono- or di-ethoxylated products, and especial preference to mono- or di-ethoxylated propargyl alcohol, and also mixtures thereof.

In the reaction step the esterification with (meth)acrylic acid or, preferably, the transesterification of the alcohol (C) with at least one, preferably one, (meth)acrylate (D) takes place in the presence of at least one, preferably one, enzyme (E) which catalyzes the transesterification.

Compounds (D) may be (meth)acrylic acid or esters of (meth)acrylic acid with a saturated alcohol, preferably saturated $C_1$-$C_{10}$ alkyl esters or $C_3$-$C_{12}$ cycloalkyl esters of (meth)acrylic acid, more preferably saturated $C_1$-$C_4$ alkyl esters of (meth)acrylic acid.

Saturated for the purposes of this text means compounds without multiple C—C bonds (except of course for the C=C double bond in the (meth)acrylic units).

Examples of compounds (D) are methyl, ethyl, n-butyl, isobutyl, n-octyl, and 2-ethylhexyl(meth)acrylate, 1,2-ethylene glycol di- and mono(meth)acrylate, 1,4-butanediol di- and mono(meth)acrylate, 1,6-hexanediol di- and mono (meth)acrylate, trimethylolpropane tri(meth)acrylate, and pentaerythritol tetra(meth)acrylate.

Particular preference is given to methyl, ethyl, n-butyl, and 2-ethylhexyl(meth)acrylate, and very particular preference to methyl, ethyl, and n-butyl(meth)acrylate.

Where the stated alcohols are optically active, they are used preferably in racemic form or as diastereomer mixtures; it is, however, also possible to use them as pure enantiomers or diastereomers, or as enantiomer mixtures.

The enzymatic esterification or transesterification with a (meth)acrylate takes place in general at 0 to 100° C., preferably 20 to 80° C., more preferably 20 to 70° C., very preferably 20 to 60° C.

Examples of enzymes (E) useful in accordance with the invention are those selected from hydrolases (E.C. 3.-.-.-), and among these especially from the esterases (E.C. 3.1.-.-), lipases (E.C. 3.1.1.3), glycosylases (E.C. 3.2.-.-), and proteases (E.C. 3.4.-.-), in free form or in a form in which they are chemically or physically immobilized on a carrier, preferably lipases, esterases or proteases, and more preferably esterases (E.C. 3.1.-.-). Very particular preference is given to Novozyme 435 (lipase from *Candida antarctica* B) or lipase from *Alcaligenes* sp., *Aspergillus* sp., *Mucor* sp., *Penicillium* sp., *Geotricum* sp., *Rhizopus* sp., *Burkholderia* sp., *Candida* sp., Pseudomonas sp., *Thermomyces* sp., or porcine pancreas, and especial preference to lipase from *Candida antarctica* B or from *Burkholderia* sp.

The enzyme content of the reaction medium is generally in the range from about 0.1 to 10% by weight, based on the alcohol (C) employed.

The reaction time depends among other things on the temperature, on the amount of the enzyme catalyst used and its activity, and on the required conversion, and also on the alcohol. The reaction time is preferably adapted so that the conversion of the hydroxyl functions comprised in the alcohol (C) that are to be reacted, i.e., the lower-substituted hydroxyl functions, is at least 70%, preferably at least 80%, more preferably at least 90%, very preferably at least 95%, in particular at least 97%, and especially at least 98%. The time sufficient for this is generally from 1 to 72 hours, preferably from 3 to 36 hours, and more preferably from 3 to 24 hours.

The molar ratio of (meth)acrylic acid compound (D) (based on the (meth)acrylic units) to alcohol (C) (based on hydroxyl groups) can be set within a wide range, such as in a ratio, for example, of from 100:1 to 1:1, preferably from 50:1 to 1:1, more preferably from 20:1 to 1:1, and very preferably from 10:1 to 1:1.

The reaction can proceed in organic solvents or mixtures thereof or without the addition of solvents. It is preferred not to add solvent. The batches are generally substantially free of water (i.e., less than 10%, preferably less than 5%, more preferably less than 1%, and very preferably less than 0.5% by volume of water added).

Suitable organic solvents are those known for these purposes, examples being tertiary monools, such as $C_3$-$C_6$ alcohols, preferably tert-butanol, tert-amyl alcohol, pyridine, poly-$C_1$-$C_4$ alkylene glycol di-$C_1$-$C_4$ alkyl ethers, preferably polyethylene glycol di-$C_1$-$C_4$ alkyl ethers, such as 1,2-dimethoxyethane, diethylene glycol dimethyl ether, polyethylene glycol dimethyl ether 500, methyl tert-butyl ether, ethyl tert-butyl ether, $C_1$-$C_4$ alkylene carbonates, especially propylene carbonate, $C_3$-$C_6$ alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and single-phase or multiphase mixtures thereof. It can be advantageous to separate alcohol or water that is liberated by means of a binary or ternary heteroazeotrope which boils as close as possible to the temperature optimum of the enzyme used. The alcohol removed in this way can then be removed by phase separation or membrane vapor separation.

As an option it is possible to add aqueous solvents to the organic solvents, thereby producing single-phase or multiphase reaction solutions, depending on the organic solvent. Examples of aqueous solvents are water and also aqueous, dilute (e.g., 10 to 100 mM) buffers, with a pH for example in the range from about 6 to 8, such as potassium phosphate buffer or TRIS-HCl buffer, for example.

The water fraction in the reaction mixture is generally 0-10% by volume. The reactants are preferably used without pretreatment (drying, water doping).

The substrates are either in solution, in suspension as solids, or in emulsion in the reaction medium. The initial concentration of the reactants is preferably in the range from about 0.1 to 20 mol/l, in particular from 0.15 to 10 mol/l or from 0.2 to 5 mol/l.

The reaction can take place continuously, in a tube reactor or in a stirred reactor cascade, for example, or batchwise.

The reaction can be conducted in all reactors suitable for such reactions. Reactors of this kind are known to the skilled worker. The reaction preferably takes place in a stirred tank reactor or fixed bed reactor.

The reaction mixture can be mixed using any desired methods. There is no need for special stirring apparatus. The reaction medium can be a single phase or a plurality of phases and the reactants are dissolved, suspended or emulsified therein, charged to the reaction vessel together if appropriate with molecular sieve, and admixed with the enzyme preparation at the start of the reaction and also, if appropriate, one or more times during the course of the reaction. The temperature during the reaction is adjusted to the desired level and can, if desired, be raised or lowered during the course of the reaction.

Where the reaction is carried out in a fixed bed reactor, said reactor is preferably packed with immobilized enzymes, the reaction mixture being pumped through a column packed with the enzyme. It is also possible to carry out the reaction in a fluidized bed, in which case the enzyme is used in a form in which it is immobilized on a carrier. The reaction mixture can be pumped continuously through the column, with the residence time and hence the desired conversion being controllable by means of the flow rate. It is also possible to pump the reaction mixture in circulation through a column, with the possibility also of distillative removal of the alcohol that is liberated at the same time, under reduced pressure.

The removal of water in the case of an esterification, or of alcohols released in a transesterification from the alkyl(meth)acrylates, takes place continuously or gradually in a manner known per se, by means of reduced pressure, azeotropic removal, absorption, pervaporation, and diffusion via membranes, for example.

Suitable for this purpose are, preferably, molecular sieves or zeolites (with a pore size, for example, in the range of about 3-10 angstroms), distillative separation or separation using appropriate semipermeable membranes.

Yet another possibility is to pass the isolated mixture of alkyl(meth)acrylate and its parent alcohol, said mixture frequently forming an azeotrope, directly to a plant for the preparation of the alkyl(meth)acrylate, so as to reuse it therein in an esterification with (meth)acrylic acid.

After the end of the reaction the reaction mixture obtainable from the esterification or transesterification can be used further without further purification or, if required, can be purified in a further step.

Generally in a purification step the enzyme used is just separated off from the reaction mixture and the reaction product is freed from any organic solvent used.

The enzyme is separated off generally by filtration, absorption, centrifugation or decanting. The enzyme separated off can subsequently be used for further reactions.

Removal of the organic solvent takes place generally by distillation, rectification or, in the case of solid reaction products, by filtration.

For the further purification of the reaction product it is also possible to carry out a chromatography.

Preferably in the purification step, however, just the enzyme used and any solvent used, or the excess (meth)acrylic acid or (meth)acrylate, are separated off.

The reaction conditions in the enzymatic esterification or transesterification are mild. The low temperatures and other mild conditions prevent the formation of by-products during the reaction, which might otherwise originate, for example, from chemical catalysts or as a result of unwanted free-radical polymerization of the (meth)acrylate used, which can otherwise be prevented only by adding stabilizers.

In the reaction regime of the invention it is possible to add additional stabilizer to the (meth)acrylic compound (D) over and above the storage stabilizer comprised in any case, examples of such additional stabilizers including hydroquinone monomethyl ether, phenothiazine, phenols, such as 2-tert-butyl-4-methylphenol or 6-tert-butyl-2,4-dimethylphenol, for example, or N-oxyls, such as 4-hydroxy-2,2,6,6-tetramethylpiperidine-N-oxyl, and 4-oxo-2,2,6,6-tetramethylpiperidine-N-oxyl, in amounts for example of from 50 to 2000 ppm. The transesterification or esterification is advantageously conducted in the presence of an oxygenous gas, preferably air or air/nitrogen mixtures.

Additionally the enzyme catalyst can be removed without problems from the end product.

If appropriate the reaction mixture can be purified if desired, purification taking place for example by filtration, distillation, rectification, chromatography, treatment with ion exchangers, adsorbents, neutral, acidic and/or alkaline washing, stripping or crystallization.

The present invention further provides the (meth)acrylates obtainable from the alcohols (C) by enzymatic esterification or transesterification. As a result of the reaction conditions of the invention, these (meth)acrylates have a DIN ISO 6271 color number below 100 APHA, preferably below 80. Furthermore they generally comprise less than 1% of by-products from rearrangement reactions of the multiple bond, from acid- or base-catalyzed side reactions.

The advantage of the (meth)acrylic esters obtained in this way in accordance with the process of the invention is that on account of their low color number they can be used with advantage in coatings applications and particularly in clearcoat materials, since, on account of their low inherent coloration, they result in reduced coloration of the coatings as compared with alcohols prepared by conventional methods.

Furthermore, coatings with the esters prepared in accordance with the invention are able to exhibit very high scratch resistance, hardness, chemical resistance, elasticity, and adhesion, on both hydrophilic and hydrophobic substrates.

The (meth)acrylic esters (F) obtainable inventively can be used with advantage as monomers or comonomers in poly(meth)acrylates or as reactive diluents in thermally curable, radiation-curable and/or dual-cure poly(meth)acrylates. Poly (meth)acrylates of this kind are suitable, for example, as binders in thermally curable, radiation-curable or dual-cure coating compositions and also in adhesives, e.g., acrylate adhesives, and also in sealants.

The present specification accordingly further provides for the use of the (meth)acrylic esters prepared by the process of the invention as reactive diluents or binders in radiation-curable or dual-cure coating materials, preferably in topcoats, more preferably in transparent clearcoat materials. The (meth)acrylic esters prepared in accordance with the invention can of course also be used as monomers in polymerizations, together if appropriate with other polymerizable monomers, such as (meth)acrylic acid, (meth)acrylic esters, styrene, butadiene, acrylonitrile, vinyl acetate, N-vinylpyrrolidone, 4-hydroxybutyl vinyl ether or N-vinylformamide, for example.

"Dual cure" means that the coating materials are curable thermally and with actinic radiation. Actinic radiation for the purposes of the present invention means electromagnetic radiation such as visible light, UV radiation or X-rays, especially UV radiation, and particulate radiation such as electron beams.

Radiation-curable binders are those which can be cured by means of actinic radiation as defined above, in particular by means of UV radiation.

The present specification further provides coating formulations comprising the (meth)acrylic esters obtainable by the process of the invention. The (meth)acrylic esters can be used both in basecoat and in topcoat materials. In view of their particular properties, especially their low color number, their use in topcoats and in radiation-cured clearcoats is preferred.

Besides the (meth)acrylic esters (F) obtainable by the process of the invention a radiation-curable composition of the invention may also comprise the following components:
(G) at least one polymerizable compound having two or more copolymerizable, ethylenically unsaturated groups,
(H) if appropriate, reactive diluents,
(I) if appropriate, photoinitiator, and
(J) if appropriate, further, typical coatings additives.

Suitable compounds (G) include radiation-curable, free-radically polymerizable compounds having a plurality of, i.e., at least two, copolymerizable, ethylenically unsaturated groups.

Compounds (G) are preferably vinyl ether compounds or (meth)acrylate compounds, particular preference being given in each case to the acrylate compounds, i.e., to the derivatives of acrylic acid.

Preferred vinyl ether and (meth)acrylate compounds (G) comprise from 2 to 20, preferably from 2 to 10, and very preferably from 2 to 6 copolymerizable, ethylenically unsaturated double bonds.

Particular preference is given to such compounds (G) having an ethylenically unsaturated double bond content of 0.1-0.7 mol/100 g, very preferably 0.2-0.6 mol/100 g.

The number-average molecular weight $M_n$ of the compounds (G), unless otherwise specified, is preferably below 15 000, more preferably 300-12 000, very preferably from 400 to 5000, and in particular 500-3000 g/mol (as determined by gel permeation chromatography using polystyrene standards and tetrahydrofuran as eluent).

As (meth)acrylate compounds mention may be made of (meth)acrylic esters and especially acrylic esters and also of vinyl ethers of polyfunctional alcohols, especially those which other than the hydroxyl groups comprise no functional groups or, if any at all, comprise ether groups. Examples of such alcohols include bifunctional alcohols, such as ethylene glycol, propylene glycol and their counterparts with higher degrees of condensation, such as diethylene glycol, triethylene glycol, dipropylene glycol, tripropylene glycol etc., 1,2-, 1,3- or 1,4-butanediol, 1,5-pentanediol, 1,6-hexanediol, 3-methyl-1,5-pentanediol, neopentyl glycol, alkoxylated phenolic compounds, such as ethoxylated and/or propoxylated bisphenols, 1,2-, 1,3- or 1,4-cyclohexanedimethanol, alcohols with a functionality of three or more, such as glycerol, trimethylolpropane, butanetriol, trimethylolethane, pentaerythritol, ditrimethylolpropane, dipentaerythritol, sorbitol, mannitol, and the corresponding alkoxylated alcohols, especially ethoxylated and/or propoxylated alcohols.

The alkoxylation products are obtainable conventionally by reacting the above alcohols with alkylene oxides, especially ethylene oxide or propylene oxide. The degree of alkoxylation per hydroxyl group is preferably from 0 to 10, i.e., 1 mol of hydroxyl group may have been alkoxylated with up to 10 mol of alkylene oxides.

As (meth)acrylate compounds mention may further be made of polyester (meth)acrylates, which are the (meth)acrylic esters or vinyl ethers of polyesterols, and also of urethane, epoxy or melamine (meth)acrylates.

Urethane (meth)acrylates, for example, are obtainable by reacting polyisocyanates with hydroxyalkyl(meth)acrylates and, if appropriate, chain extenders such as diols, polyols, diamines, polyamines, or dithiols or polythiols.

The urethane (meth)acrylates preferably have a number-average molar weight $M_n$ of from 500 to 20 000, in particular from 750 to 10 000, and more preferably from 750 to 3000 g/mol (as determined by gel permeation chromatography using polystyrene standards).

The urethane (meth)acrylates preferably contain from 1 to 5, more preferably from 2 to 4, mol of (meth)acrylic groups per 1000 g of urethane (meth)acrylate.

Epoxy(meth)acrylates are obtainable by reacting epoxides with (meth)acrylic acid. Examples of suitable epoxides include epoxidized olefins or glycidyl ethers, e.g., bisphenol A diglycidyl ether or aliphatic glycidyl ethers, such as butanediol diglycidyl ether.

Melamine (meth)acrylates are obtainable by reacting melamine with (meth)acrylic acid or the esters thereof.

The epoxy(meth)acrylates and melamine (meth)acrylates preferably have a number-average molar weight $M_n$ of from 500 to 20 000, more preferably from 750 to 10 000 g/mol and very preferably from 750 to 3000 g/mol; the amount of (meth) acrylic groups is preferably from 1 to 5, more preferably from 2 to 4, per 1000 g of epoxy (meth)acrylate or melamine (meth)acrylate (as determined by gel permeation chromatography using polystyrene standards and tetrahydrofuran as eluent).

Also suitable are carbonate (meth)acrylates, comprising on average preferably from 1 to 5, in particular from 2 to 4, more preferably 2 or 3 (meth)acrylic groups and, with very particular preference, 2 (meth)acrylic groups.

The number-average molecular weight $M_n$ of the carbonate (meth)acrylates is preferably less than 3000 g/mol, more preferably less than 1500 g/mol, very preferably less than 800 g/mol (as determined by gel permeation chromatography using polystyrene standards and tetrahydrofuran as solvent).

The carbonate (meth)acrylates are readily obtainable by transesterification of carbonic esters with polyhydric, preferably dihydric, alcohols (diols, e.g., hexanediol) and subsequent esterification of the free OH groups with (meth)acrylic acid or else transesterification with (meth)acrylic esters, as described for example in EP-A 92 269. They are also obtainable by reacting phosgene, urea derivatives with polyhydric alcohols, e.g., dihydric alcohols.

Suitable reactive diluents (compounds (H)) include radiation-curable, free-radically or cationically polymerizable compounds having only one ethylenically unsaturated copolymerizable group.

Examples that may be mentioned include $C_1$-$C_{20}$ alkyl (meth)acrylates, vinylaromatics having up to 20 carbon atoms, vinyl esters of carboxylic acids comprising up to 20 carbon atoms, ethylenically unsaturated nitriles, vinyl ethers of alcohols comprising 1 to 10 carbon atoms, α,β-unsaturated carboxylic acids and their anhydrides, and aliphatic hydrocarbons having from 2 to 8 carbon atoms and 1 or 2 double bonds. Preferred alkyl(meth)acrylates are those with a $C_1$-$C_{10}$ alkyl radical, such as methyl methacrylate, methyl acrylate, n-butyl acrylate, ethyl acrylate, and 2-ethylhexyl acrylate.

In particular, mixtures of the alkyl(meth)acrylates are also suitable.

Examples of vinyl esters of carboxylic acids having 1 to 20 carbon atoms are vinyl laurate, vinyl stearate, vinyl propionate, and vinyl acetate.

Examples of α,β-unsaturated carboxylic acids and their anhydrides include acrylic acid, methacrylic acid, fumaric acid, crotonic acid, itaconic acid, maleic acid, and maleic anhydride, preferably acrylic acid.

Examples of suitable vinylaromatic compounds include vinyltoluene, α-butylstyrene, 4-n-butylstyrene, 4-n-decylstyrene, and, preferably, styrene.

Examples of nitriles are acrylonitrile and methacrylonitrile.

Examples of suitable vinyl ethers include vinyl methyl ether, vinyl isobutyl ether, vinyl hexyl ether, and vinyl octyl ether.

As nonaromatic hydrocarbons having 2 to 8 carbon atoms and one or two olefinic double bonds mention may be made of butadiene, isoprene, and of ethylene, propylene, and isobutylene.

It is further possible to employ N-vinylformamide, N-vinylpyrrolidone, and N-vinylcaprolactam.

As photoinitiators (I) it is possible to use photoinitiators known to the skilled worker, examples being UV photoinitiators, e.g., those in "Advances in Polymer Science", Volume 14, Springer Berlin 1974 or in K. K. Dietliker, Chemistry and Technology of UV- and EB-Formulation for Coatings, Inks and Paints, Volume 3; Photoinitiators for Free Radical and Cationic Polymerization, P. K. T. Oldring (ed.), SITA Technology Ltd, London.

Suitable examples include mono- or bisacylphosphine oxides such as Irgacure 819 (bis(2,4,6-trimethylbenzoyl)phenylphosphine oxide), as described for example in EP-A 7 508, EP-A 57 474, DE-A 196 18 720, EP-A 495 751 or EP-A 615 980, examples being 2,4,6-trimethylbenzoyldiphenylphosphine oxide (Lucirin® TPO), ethyl 2,4,6-trimethylbenzoylphenylphosphinate, benzophenones, hydroxyacetophenones, phenylglyoxylic acid and derivatives thereof, or mixtures of these photoinitiators. Examples that may be mentioned include benzophenone, acetophenone, acetonaphthoquinone, methyl ethyl ketone, valerophenone, hexanophenone, α-phenyl-butyrophenone, p-morpholinopropiophenone, dibenzosuberone, 4-morpholinobenzophenone, 4-morpholinodeoxybenzoin, p-diacetylbenzene, 4-aminobenzophenone, 4'-methoxyacetophenone, β-methylanthraquinone, tert-butylanthraquinone, anthraquinonecarboxylic esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethylthioxanthone, 2,4-diethylthioxanthone, 2,4-diisopropylthioxanthone, 2,4-dichlorothioxanthone, benzoin, benzoin isobutyl ether, chloroxanthenone, benzoin tetrahydropyranyl ether, benzoin methyl ether, benzoin ethyl ether, benzoin butyl ether, benzoin isopropyl ether, 7H-benzoin methyl ether, benz[de]anthracen-7-one, 1-naphthaldehyde, 4,4'-bis(dimethylamino)benzophenone, 4-phenylbenzophenone, 4-chlorobenzophenone, Michler's ketone, 1-acetonaphthone, 2-acetonaphthone, 1-benzoylcyclohexan-1-ol, 2-hydroxy-2,2-dimethylacetophenone, 2,2-dimethoxy-2-phenylacetophenone, 2,2-diethoxy-2-phenylacetophenone, 1,1-dichloroacetophenone, 1-hydroxyacetophenone, acetophenone dimethyl ketal, o-methoxybenzophenone, triphenylphosphine, tri-o-tolylphosphine, benz[α]anthracene-7,12-dione, 2,2-diethoxyacetophenone, benzil ketals, such as benzil dimethyl ketal, 2-methyl-1-[4-(methylthio)phenyl]-2-morpholinopropan-1-one, anthraquinones such as 2-methylanthraquinone, 2-ethylanthraquinone, 2-tert-butylanthraquinone, 1-chloroanthraquinone, 2-amylanthraquinone, and 2,3-butanedione.

Also suitable are nonyellowing or low-yellowing photoinitiators of the phenylglyoxalic ester type, as described in DE-A 198 26 712, DE-A 199 13 353 or WO 98/33761.

Among said photoinitiators phosphine oxides, α-hydroxy ketones, and benzophenones are preferred.

In particular it is also possible to use mixtures of different photoinitiators.

The photoinitiators can be used alone or in combination with a photopolymerization promoter, of the benzoic acid, amine or similar type, for example.

Also conceivable is the use of IR photoinitiators.

IR photoinitiators comprise a sensitizer/coinitiator mixture. As sensitizer dye it is common to use dyes, more particularly cyanine, xanthylium or thiazine dyes, and as coinitiators, for example, boranate salts, sulfonium salts, iodonium salts, sulfones, peroxides, pyridine N-oxides or halomethyltriazines.

As further, typical coatings additives (J) it is possible to make use, for example, of antioxidants, oxidation inhibitors, stabilizers, activators (accelerators), fillers, pigments, dyes, devolatilizers, luster agents, antistats, flame retardants, thickeners, thixotropic agents, leveling assistants, binders, antifoams, fragrances, surfactants, viscosity modifiers, plasticizers, tackifying resins (tackifiers), chelating agents or compatibilizers.

Examples of accelerators for thermal aftercure that can be used include tin octoate, zinc octoate, dibutyltin laurate, and diazabicyclo[2.2.2]octane.

It is also possible to add one or more photochemically and/or thermally activatable initiators, such as potassium peroxodisulfate, dibenzoyl peroxide, cyclohexanone peroxide, di-tert-butyl peroxide, azobisisobutyronitrile, cyclohexylsulfonyl acetyl peroxide, diisopropyl percarbonate, tert-butyl peroctoate or benzpinacol, and also, for example, those thermally activatable initiators which have a half-life at 80° C. of more than 100 hours, such as di-t-butyl peroxide, cumene hydroperoxide, dicumyl peroxide, t-butyl perbenzoate, silylated pinacols, available commercially, for example, under the trade name ADDID 600 from Wacker, or hydroxyl-containing amine N-oxides, such as 2,2,6,6-tetramethylpiperidine-N-oxyl, 4-hydroxy-2,2,6,6-tetramethylpiperidine-N-oxyl etc.

Further examples of suitable thermally activatable initiators are described in "Polymer Handbook", 2nd ed., Wiley & Sons, New York.

Suitable thickeners besides free-radically (co)polymerized (co)polymers include customary organic and inorganic thickeners such as hydroxymethylcellulose or bentonites.

Examples of chelating agents which can be used include ethylenediamineacetic acid and salts thereof and also β-diketones.

Suitable fillers comprise silicates, examples being silicates obtainable by hydrolysis of silicon tetrachloride such as Aerosil® from Degussa, silicious earth, talc, aluminum silicates, magnesium silicates, calcium carbonates, etc.

Suitable stabilizers comprise typical UV absorbers such as oxanilides, triazines, and benzotriazole (the latter obtainable as Tinuvin® grades from Ciba-Spezialitätenchemie), and benzophenones. They can be used alone or together with suitable free-radical scavengers, examples being sterically hindered amines such as 2,2,6,6-tetramethyl-piperidine, 2,6-di-tert-butylpiperidine or derivatives thereof, e.g., bis(2,2,6, 6-tetramethyl-4-piperidyl) sebacate. Stabilizers are normally used in amounts of from 0.1 to 5.0% by weight, based on the solid components present in the formulation.

Examples of stabilizers which are additionally suitable include N-oxyls, such as 4-hydroxy-2,2,6,6-tetramethylpiperidine-N-oxyl, 4-oxo-2,2,6,6-tetramethylpiperidine-N-oxyl, 4-acetoxy-2,2,6,6-tetramethylpiperidine-N-oxyl, 2,2,6,6-tetramethylpiperidine-N-oxyl, 4,4',4"-tris(2,2,6,6-tetramethylpiperidine-N-oxyl) phosphite or 3-oxo-2,2,5,5-tetramethylpyrrolidine-N-oxyl, phenols and naphthols, such as p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butyl phenol (2,6-tert-butyl-p-cresol) or 4-tert-butyl-2,6-dimethylphenol, quinones, such as hydroquinone or hydroquinone monomethyl ether, aromatic amines, such as N,N-diphenylamine, N-nitrosodiphenylamine, phenylenediamines, such as N,N'-dialkyl-para-phenylenediamine, where the alkyl radicals can be identical or different, consist independently of 1 to 4 carbon atoms, and be straight-chain or branched, hydroxylamines, such as N,N-diethylhydroxylamine, urea derivatives, such as urea or thiourea, phosphorus compounds, such as triphenylphosphine, triphenyl phosphite or triethyl phosphite, or sulfur compounds, such as diphenyl sulfide or phenothiazine, for example.

Examples of typical compositions for radiation-curable materials are:
(F) 20-100%, preferably 40-90%, more preferably 50-90%, and in particular 60-80% by weight,
(G) 0-60%, preferably 5-50%, more preferably 10-40%, and in particular 10-30% by weight,
(H) 0-50%, preferably 5-40%, more preferably 6-30%, and in particular 10-30% by weight,
(I) 0-20%, preferably 0.5-15%, more preferably 1-10%, and in particular 2-5% by weight, and
(J) 0-50%, preferably 2-40%, more preferably 3-30%, and in particular 5-20% by weight,
with the proviso that (F), (G), (H), (I), and (J) together make 100% by weight.

The substrates are coated in accordance with methods which are conventional and are known to the skilled worker, applying at least one coating material to the target substrate in the desired thickness and removing any volatile constituents comprised in the coating material, with heating if appropriate. This operation can be repeated one or more times as desired. Application to the substrate may be made in a known way, for example, by spraying, troweling, knifecoating, brushing, rolling, roller coating, flow coating, laminating, injection backmolding or coextrusion. The coating thickness is generally in a range from about 3 to 1000 g/m² and preferably from 10 to 200 g/m².

Further disclosed is a method of coating substrates which comprises applying the coating material to the substrate and drying it if appropriate, curing it with electron beams or by UV exposure under an oxygenous atmosphere or, preferably, under inert gas, if appropriate at temperatures up to the level of the drying temperature.

In addition to or instead of thermal drying, drying may also take place by means of NIR radiation, which refers here to electromagnetic radiation in the wavelength range from 760 nm to 2.5 μm, preferably from 900 to 1500 nm.

Where two or more films of the coating composition are applied atop one another, it is possible for each coating operation to be followed by thermal and/or NIR drying and radiation curing, if appropriate.

Examples of suitable radiation sources for radiation curing include low-pressure, medium-pressure, and high-pressure mercury lamps, fluorescent tubes, pulsed lamps, metal halide lamps, electronic flash installations, which allow radiation curing without photoinitiator, or excimer sources. Radiation curing is accomplished by exposure to high-energy radiation, i.e., UV radiation or daylight, preferably light in the wavelength (λ) range of from 200 to 700 nm, more preferably from 200 to 500 nm, and very preferably from 250 to 400 nm, or by bombardment with high-energy electrons (electron beams; 150 to 300 keV). Examples of radiation sources used include high-pressure mercury vapor lamps, lasers, pulsed lamps (flash light), halogen lamps, or excimer sources. The radiation dose normally sufficient for crosslinking in the case of UV curing is in the range from 80 to 3000 mJ/cm².

It is of course also possible to use two or more radiation sources for curing, e.g., from two to four.

These sources may also each emit in different wavelength regions.

Irradiation can be carried out if appropriate in the absence of oxygen as well, such as under an inert gas atmosphere, for example. Suitable inert gases include, preferably, nitrogen, noble gases, carbon dioxide or combustion gases. Irradiation may also take place with the coating material covered with transparent media. Examples of transparent media include polymeric films, glass or liquids, such as water. Particular preference is given to irradiation in the manner described in DE-A1 199 57 900.

The present invention further provides substrates coated with a multicoat paint system of the invention.

The thickness of such a film to be cured as described can be from 0.1 μm up to several mm, preferably from 1 to 2000 μm, more preferably from 5 to 1000 μm, very preferably from 10 to 500 μm, and in particular from 10 to 250 μm.

In view of their relatively low coloring, the (meth)acrylic esters prepared in accordance with the invention can also be used with advantage in a thermally induced (free-radical) (co)polymerization.

Examples of monomers which may be copolymerized with the (meth)acrylic esters prepared in accordance with the invention include for example $C_1$-$C_{20}$ alkyl (meth)acrylates, vinylaromatics having up to 20 carbon atoms, vinyl esters of carboxylic acids comprising up to 20 carbon atoms, ethylenically unsaturated nitriles, vinyl ethers of alcohols comprising 1 to 10 carbon atoms, and aliphatic hydrocarbons having 2 to 8 carbon atoms and 1 or 2 double bonds.

Preferred (meth)acrylic acid alkyl esters are those with a $C_1$-$C_{10}$ alkyl radical, such as methyl methacrylate, methyl acrylate, n-butyl acrylate, ethyl acrylate and branched alkyl derivatives such as 2-ethylhexyl acrylate.

In particular, mixtures of the (meth)acrylic acid alkyl esters as well are suitable.

Vinyl esters of carboxylic acids having 1 to 20 carbon atoms are for example vinyl laurate, vinyl stearate, vinyl propionate and vinyl acetate.

Examples of suitable vinylaromatic compounds include vinyltoluene, α-butylstyrene, 4-n-butylstyrene, 4-n-decylstyrene, and, preferably, styrene.

Examples of nitriles are acrylonitrile and methacrylonitrile.

Examples of suitable vinyl ethers are vinyl methyl ether, vinyl isobutyl ether, vinyl hexyl ether and vinyl octyl ether.

As nonaromatic hydrocarbons having 2 to 8 carbon atoms and one or two olefinic double bonds mention may be made of butadiene, isoprene, and also ethylene, propylene and isobutylene.

A frequent method, though not the only one, for preparing such (co)polymers is that of free-radical or ionic (co)polymerization in a solvent or diluent.

The free-radical (co)polymerization of such monomers takes place for example in aqueous solution in the presence of polymerization initiators which break down into free radicals under polymerization conditions, examples being peroxodisulfates, $H_2O_2$ redox systems or hydroxy peroxides, such as tert-butyl hydroperoxide or cumene hydroperoxide, for example. The (co)polymerization may be performed within a wide temperature range, if appropriate under reduced pressure or else under elevated pressure, generally at temperatures up to 100° C. The pH of the reaction mixture is commonly set in the range from 4 to 10.

Alternatively the (co)polymerization can be carried out in another way known per se to the skilled worker, continuously or batchwise, in the form for example of a solution, precipitation, water-in-oil emulsion, inverse emulsion, suspension or inverse suspension polymerization.

In the (co)polymerization the monomer/monomers is/are (co)polymerized using free-radical polymerization initiators, examples being azo compounds which break down into free radicals, such as 2,2'-azobis(isobutyronitrile), 2,2'-azobis(2-amidinopropane) hydrochloride or 4,4'-azobis(4'-cyanopentanoic acid) or dialkyl peroxides, such as di-tert-amyl peroxide, aryl alkyl peroxides, such as tert-butyl cumyl peroxide, alkyl acyl peroxides, such as tert-butyl peroxy-2-ethylhexanoate, peroxydicarbonates, such as di(4-tert-butylcyclohexyl) peroxydicarbonate, or hydroperoxides.

The stated compounds are generally used in the form of aqueous solutions or aqueous emulsions, the lower concentration being determined by the amount of water that is acceptable in the (co)polymerization and the upper concentration by the solubility of the respective compound in water.

Examples of compounds which can be used as solvents or diluents include water, alcohols, such as methanol, ethanol, n- or isopropanol, n- or isobutanol, or ketones, such as acetone, ethyl methyl ketone, diethyl ketone or isobutyl methyl ketone. Particular preference is given to nonpolar solvents such as, for example, xylene and its isomer mixtures, Shellsol® A, and solvent naphtha.

In one preferred embodiment the monomers are premixed and initiator together if appropriate with further additions is added as a solvent solution. One particularly preferred embodiment is described in WO 01/23484, particularly therein on page 10, line 3 to line 24.

If appropriate the (co)polymerization can be conducted in the presence of polymerization regulators, such as hydroxylammonium salts, chlorinated hydrocarbons and thio compounds, such as tert-butyl mercaptan, thioglycolic acid ethylacrylic esters, mercaptoethynol, mercaptopropyltrimethoxysilane, dodecyl mercaptan, tert-dodecyl mercaptan or alkali metal hypophosphites, for example. In the (co)polymerization these regulators can be used, for example, in amounts of from 0 to 0.8 part by weight, based on 100 parts by weight of the monomers to be (co)polymerized, and they lower the molar mass of the resultant (co)polymer.

For emulsion polymerization it is possible to use dispersants, ionic and/or nonionic emulsifiers and/or protective colloids, and/or stabilizers, as surface-active compounds.

Suitable such compounds include not only the protective colloids that are normally used for implementing emulsion polymerizations, but also emulsifiers.

Examples of suitable protective colloids include polyvinyl alcohols, cellulose derivatives, and vinylpyrrolidone comprising copolymers. An exhaustive description of further suitable protective colloids can be found in Houben-Weyl, Methoden der organischen Chemie, volume XIV/1, Macromolecular compounds, Georg-Thieme-Verlag, Stuttgart, 1969, pp. 411 to 420. It will be appreciated that mixtures of emulsifiers and/or protective colloids can also be used. As dispersants it is preferred to use exclusively emulsifiers, whose relative molecular weights, unlike those of the protective colloids, are usually below 1000. They may be anionic, cationic or nonionic in nature. As will be appreciated it is necessary, when using mixtures of surface-active substances, that the individual components be compatible with one another, something which in case of doubt can be checked by means of a few preliminary tests. Generally speaking, anionic emulsifiers are compatible with one another and with nonionic emulsifiers.

The same also applies to cationic emulsifiers, whereas anionic and cationic emulsifiers are usually incompatible with one another. Examples of customary emulsifiers include ethoxylated mono-, di- and tri-alkylphenols (EO units: 3 to 100, alkyl: $C_4$ to $C_{12}$), ethoxylated fatty alcohols (EO units: 3 to 100, alkyl: $C_8$ to $C_{18}$), and also alkali metal and ammonium salts of alkyl sulfates (alkyl: $C_8$ to $C_{16}$) of sulfuric monoesters with ethoxylated alkylphenols (EO units: 3 to 100, alkyl: $C_4$ to $C_{12}$), of alkylsulfonic acids (alkyl: $C_{12}$ to $C_{18}$) and of alkylarylsulfonic acids (alkyl: $C_8$ to $C_{18}$). Further suitable emulsifiers, such as sulfosuccinic esters, can be found in Houben-Weyl, Methoden der organischen Chemie, volume XIV/1, Macromolecular compounds, Georg-Thieme Verlag, Stuttgart, 1961, pages 192 to 208.

In general the amount of dispersant used is from 0.5 to 6%, preferably from 1 to 3% by weight, based on the monomers for free-radical polymerization.

Examples of (meth)acrylate-containing dispersions are n-butyl acrylate/acrylonitrile dispersions, which are employed as adhesives, and n-butyl acrylate/butadiene/styrene dispersions.

The polymer dispersions in which (meth)acrylic esters prepared in accordance with the invention are used may additionally be subjected to chemical and/or physical deodorization.

The copolymers obtainable with the (meth)acrylic esters prepared in accordance with the invention generally have a relatively low color number, which is advantageous in the coatings sector. The described copolymers can then be reacted in a manner known per se with amino resins, for example, such as melamine, to form crosslinked film-forming resins, as described for example in EP 738740 or EP 675141.

The coating materials of the invention are suitable with particular preference as or in exterior coatings, i.e., those applications which are exposed to daylight, preferably on buildings or parts of buildings, interior coatings, traffic markings, and coatings on vehicles and aircraft. The coatings are employed in particular as wood, paper or plastics coatings, for woodblock flooring or furniture for example.

The invention further provides for the use of the products obtained in accordance with the invention as an intermediate for bright electroplating additives. Their color number, which is reduced relative to that of products obtainable conventionally, makes them inordinately suitable for this application.

The process of the invention allows the preparation of (meth)acrylic esters (F) in high chemical and space/time yield and under mild conditions and with good color numbers. Despite not using activated (meth)acrylic acid compounds, the desired products are obtained in a targeted way, with high selectivity, and are substantially free from by-products.

The examples which follow are intended to illustrate the qualities of the invention without, however, restricting it.

EXAMPLES

Parts in this document, unless specified otherwise, are to be understood as referring to parts by weight.

Golpanol® PME is a commercially available product of BASF AG, Ludwigshafen, Germany. It comprises a mixture of mono- and di-ethoxylated propargyl alcohol.

Example 1

Transesterification of
Golpanol® PME with different excesses of methyl acrylate

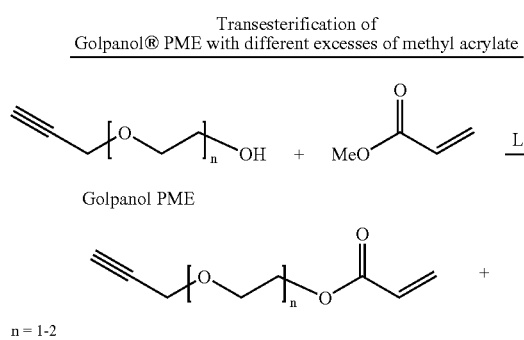

Golpanol® PME (5 mmol, 501 mg) was shaken with methyl acrylate, 25 mg of Novozym® 435 (Lipase from *Candida antarctica* B), and 1.0 g of 5 Å molecular sieve at 40° C. for 24 h and the conversion was determined by means of gas chromatography.

| Amount of methyl acrylate [mmol] | Conversion [%] |
|---|---|
| 50 | 100 |
| 40 | 100 |
| 30 | 100 |
| 20 | 99 |
| 20 (no enzyme) | 10 |
| 10 | 92 |

Example 2

Preparative batch with Golpanol PME

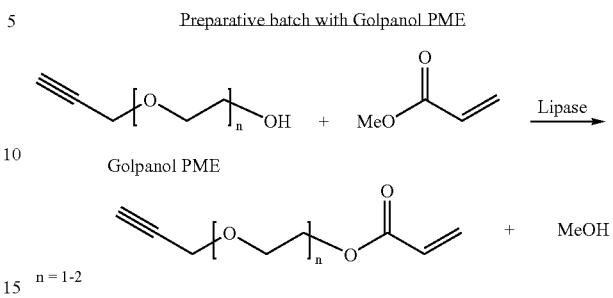

A 4 l round-bottomed flask with top-mounted reflux condenser was charged with 1377 g of methyl acrylate (16.0 mol), 400.5 g of Golpanol® PME (4.0 mol, Hazen color number: 47 (APHA)), 800 g of 5 Å molecular sieve, and 50 mg of hydroquinone monomethyl ether and the reaction was initiated by addition of 20.0 g of Novozym® 435. After 7 h of stirring at 40° C. the solids were removed via a suction filter. The excess methyl acrylate was removed on a rotary evaporator (40° C., 6 mbar). According to analysis by gas chromatography the degree of esterification of the alcohol was 99.5%. This gave 557 g (93% yield) of 2-propargyloxethyl acrylate as a clear, pale yellowish liquid having a Hazen color number of 79 (APHA, in accordance with DIN ISO 6271).

Example 3

Reaction of propargyl alcohol

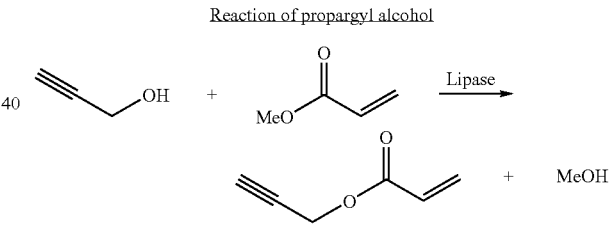

Propargyl alcohol (5 mmol, 295 µl) was shaken with 50 mmol of methyl acrylate (4.51 ml), 25 mg of Novozym® 435, and, if appropriate, 1.0 g of 5 Å molecular sieve at 40° C. for 24 h and the conversion was determined by means of GC.

| Molecular sieve added | Conversion [%] |
|---|---|
| none | 58 |
| added | 95 |

The invention claimed is:

1. A process for preparing a (meth)acrylic ester (F), comprising:
    subjecting (C) propargyl alcohol or a mono- or di-ethoxylated product thereof, or a mixture thereof, to transesterification with (D) at least one (meth)acrylic ester, in the presence of (E) a lipase B from *Candida antarctica*, wherein
the (meth)acrylic ester (D) comprises a saturated $C_1$-$C_{10}$ alkyl ester or $C_3$-$C_{12}$ cycloalkyl ester of (meth)acrylic acid, and
the molar ratio of the (meth)acrylic ester (D), based on (meth)acrylic units, to the (C) propargyl alcohol or a mono- or di-ethoxylated product thereof, or a mixture thereof, based on hydroxyl groups, is from 20:1 to 1:1.

2. The process of claim 1, wherein (C) is propargyl alcohol.

3. The process of claim 1, wherein (C) comprises a mono-ethoxylated product of propargyl alcohol.

4. The process of claim 1, wherein (C) comprises a di-ethoxylated product of propargyl alcohol.

5. The process of claim 1, wherein the degree of transesterification of the alcohol (C) is 92% or more.

6. The process of claim 1, wherein the (meth)acrylic ester (D) comprises a saturated $C_1$-$C_{10}$ alkyl ester.

7. The process of claim 1, wherein the (meth)acrylic ester (D) is comprises a $C_3$-$C_{12}$ cycloalkyl ester of (meth)acrylic acid.

8. The process of claim 1, wherein the molar ratio of the (meth)acrylic ester (D), based on (meth)acrylic units, to the (C) propargyl alcohol or a mono- or di-ethoxylated product thereof, or a mixture thereof, based on hydroxyl groups, is from 10:1 to 1:1.

9. The process of claim 1, which is conducted in the absence of a solvent.

* * * * *